United States Patent
Bovi

(10) Patent No.: US 10,161,845 B2
(45) Date of Patent: Dec. 25, 2018

(54) METHOD FOR MONITORING A PARTICULATE FILTER

(71) Applicant: DELPHI TECHNOLOGIES IP LIMITED, St. Michael (BB)

(72) Inventor: Philippe Bovi, Havange (FR)

(73) Assignee: DELPHI TECHNOLOGIES IP LIMITED (BB)

( * ) Notice: Subject to any disclaimer, the term of this patent is extended or adjusted under 35 U.S.C. 154(b) by 218 days.

(21) Appl. No.: 15/041,357

(22) Filed: Feb. 11, 2016

(65) Prior Publication Data

US 2016/0238508 A1 Aug. 18, 2016

(51) Int. Cl.
*G01N 15/06* (2006.01)
*F01N 9/00* (2006.01)
(Continued)

(52) U.S. Cl.
CPC ......... *G01N 15/0656* (2013.01); *F01N 3/021* (2013.01); *F01N 9/002* (2013.01); *F01N 9/005* (2013.01); *F01N 11/00* (2013.01); *G01M 15/102* (2013.01); *F01N 2550/04* (2013.01); *F01N 2560/05* (2013.01); *F01N 2560/14* (2013.01); *F01N 2560/20* (2013.01);
(Continued)

(58) Field of Classification Search
CPC ....... G01N 15/0656; G01N 2015/0046; G01N 15/1606; F01N 3/021; F01N 9/002; F01N 9/005; F01N 11/00; F01N 2250/04; F01N 2560/05; F01N 2560/14; F01N 2560/20; F01N 2900/0416; F01N 2900/0418; F01N 2900/0601; F01N 2900/1606; F01N 2550/04; G01M 15/102; Y02T 10/20; Y02T 10/47

USPC ........................................................ 73/23.33
See application file for complete search history.

(56) References Cited

U.S. PATENT DOCUMENTS 7,278,304 B2 * 10/2007 Zanini-Fisher ......... F01N 11/00
                                                                                     701/31.1
8,561,388 B2 * 10/2013 Yahata .................. F01N 11/007
                                                                                     60/274
(Continued)

FOREIGN PATENT DOCUMENTS

JP          2007132290 A  *  5/2007
JP          2011231728 A    11/2011

OTHER PUBLICATIONS

GB 1502317.9 Search Report.

*Primary Examiner* — Lisa Caputo
*Assistant Examiner* — Irving A Campbell
(74) *Attorney, Agent, or Firm* — Joshua M. Haines

(57) ABSTRACT

A diagnostic method for a particulate filter in an exhaust line of an internal combustion engine is presented. The exhaust gas stream downstream of the particulate filter is monitored by a downstream soot sensor having a characteristic sensor cycle; and the accumulation of soot at an upstream soot sensor is monitored over a respective sensor cycle of the downstream soot sensor. The particulate filter operating status is decided on the basis of the information of the downstream and upstream soot sensors. The amount of accumulated soot is determined based on the sensor cycles of the upstream soot sensor, and may be expressed as a soot loading level or as a number of sensor cycles. The efficiency of the particulate filter may be determined from the respective number of sensor cycles of the soot sensors.

11 Claims, 4 Drawing Sheets

(51) Int. Cl.
*F01N 3/02* (2006.01)
*F01N 11/00* (2006.01)
*G01M 15/10* (2006.01)
*F01N 3/021* (2006.01)
*G01N 15/00* (2006.01)

(52) U.S. Cl.
CPC ........... *F01N 2900/0416* (2013.01); *F01N 2900/0418* (2013.01); *F01N 2900/0601* (2013.01); *F01N 2900/1606* (2013.01); *G01N 2015/0046* (2013.01); *Y02T 10/20* (2013.01); *Y02T 10/47* (2013.01)

(56) References Cited

U.S. PATENT DOCUMENTS

| | | |
|---|---|---|
| 2008/0059093 A1 | 3/2008 | Bromberg et al. |
| 2009/0094963 A1 | 4/2009 | Mizoguchi et al. |
| 2010/0101409 A1 | 4/2010 | Bromberg et al. |
| 2011/0120088 A1* | 5/2011 | George ............... F01N 3/021 60/274 |
| 2013/0014641 A1 | 1/2013 | Takaoka et al. |
| 2013/0036805 A1 | 2/2013 | Yoshioka |
| 2013/0192208 A1 | 8/2013 | Shibata et al. |
| 2014/0150406 A1* | 6/2014 | Goodwin ............. F01N 11/00 60/274 |

* cited by examiner

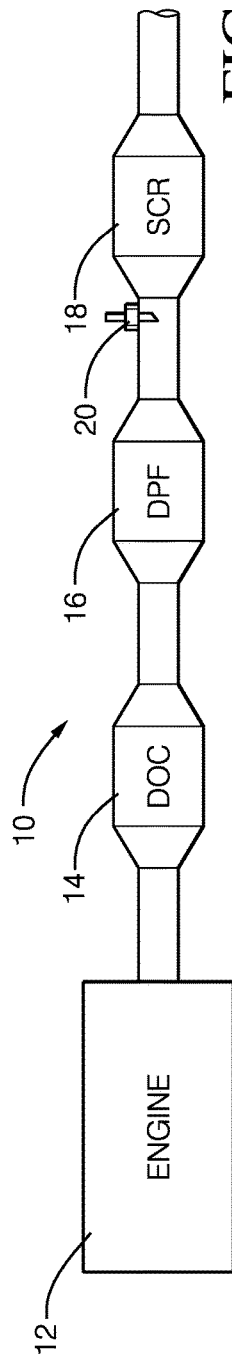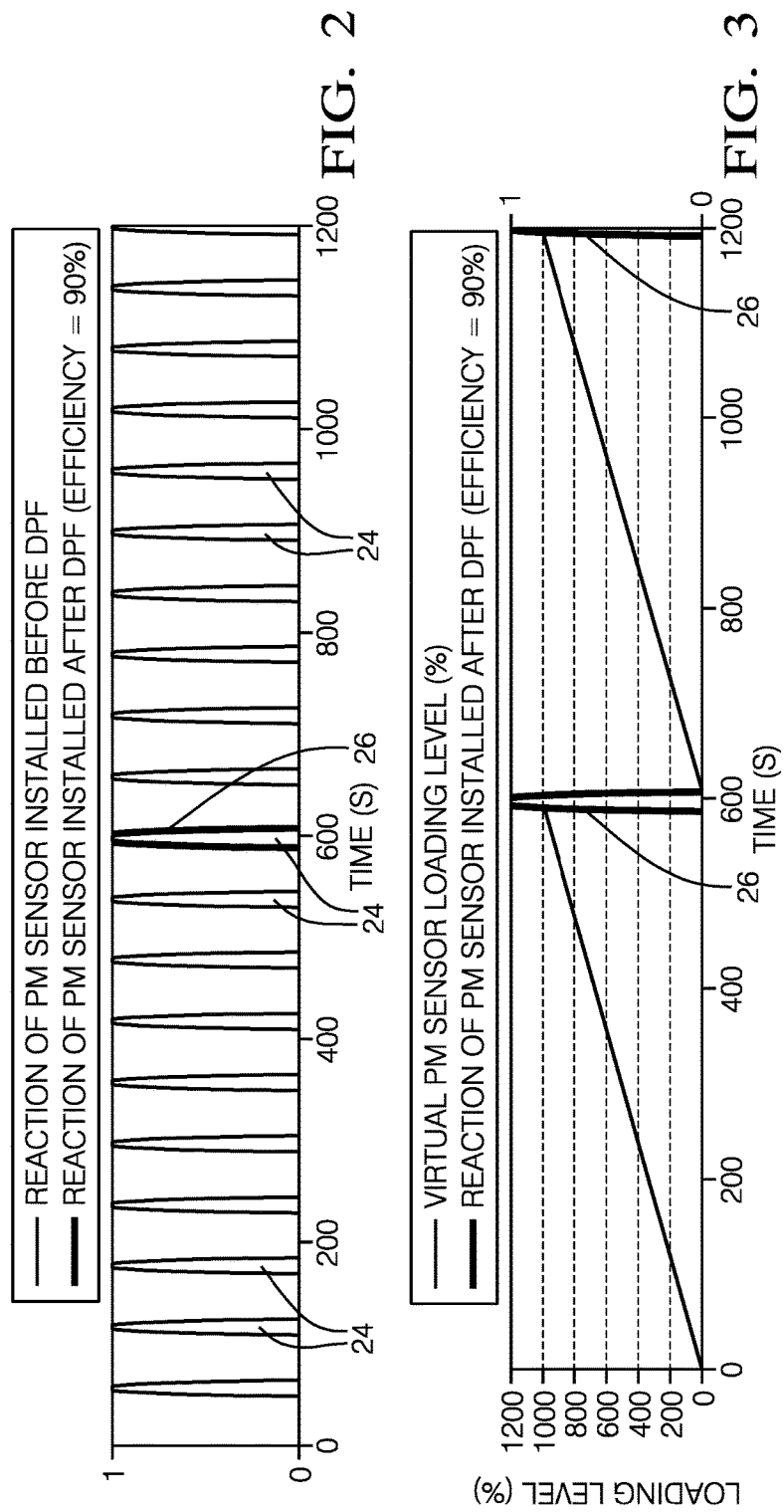

METHOD FOR MONITORING A PARTICULATE FILTER

CROSS REFERENCE TO RELATED APPLICATIONS

This application claims the benefit of GB Patent Application No. 1502317.9 filed on Feb. 12, 2015, the entire disclosure of which is hereby incorporated by reference in its entirety.

FIELD OF THE INVENTION

The present invention generally relates to exhaust gas treatment in internal combustion engines by means of particulate filters and more particularly to the monitoring/diagnostic of such particulate filters.

BACKGROUND OF THE INVENTION

Modern internal combustion engines are featured with various exhaust after treatment devices to reduce the toxicity of emissions from the engine. Components typically used for treating the exhaust gas include:
- a catalytic converter to break down gaseous pollutants in the exhaust gas;
- a particulate filter (or soot filter) to remove the fine, solid particles in the exhaust gas (especially in diesel engines).

As it is well known, exhaust gas treatment in diesel engines (operating with excess air) is nowadays carried out by means of an oxidation-type catalytic converter (also called Diesel Oxidation Catalyst or DOC). The role of the DOC is to break down pollutants in the exhaust stream into less harmful component.

The particulate filter (typically referred to as Diesel Particulate Filter in diesel engines—DPF), in turn, is designed to remove diesel particulate matter or soot from the exhaust gas. While such devices can attain great efficiency rates, they require a regular monitoring of their operating status and periodical cleaning.

The emission legislations in the US and Europe have introduced the need for the application of DPFs. In this connection, in order to fulfill future on-board diagnostic legislations (OBD), which require more stringent requirements on monitoring the particulate filter, it is necessary to detect the soot amount released by the DPF.

In this connection, Thorsten Ochs, et al., in "*Particulate Matter Sensor for On Board Diagnostics (OBD) of Diesel Particulate Filters (DPF)*", SAE International, 2010-01-0307 (December 2010), pages 73 to 81, describe an OBD concept algorithm for monitoring a DPF using a resistive-type soot sensor directly placed downstream of the DPF.

Such resistive soot sensor is based on a multi-layer ceramic technology and comprises inter-digitated electrodes with an initially infinite electrical resistance. During sensor operation soot particles are collected onto the sensor and form conductive paths between the electrodes, giving rise to a current dependent on the collected soot mass. The accumulated soot particles are eliminated by burning during a regeneration phase, before a new measuring cycle starts.

The signal of interest, which is representative of the soot flow in the exhaust, is actually the time between the start of sensor operation (following a regeneration) and the reaching of a predetermined current threshold, which is referred to as the "response time" of the sensor. Hence, in practice, the response time correlates with the soot flow in the exhaust gas and has been used for OBD diagnostic.

The DPF OBD concept algorithm proposed by Ochs et al. relies on a limit DPF model, i.e. a model representing a DPF in the least acceptable operating condition. A model-based expected response time is calculated based on a simulated engine-out soot mass flow and taking into account the limit DPF model. The DPF OBD concept algorithm then compares the expected response time with the measured response time and can thereon draw conclusions about the operating status of the DPF. If the measured response time is lower than the predicted response time, the DPF is indicated as faulty.

OBJECT OF THE INVENTION

The object of the present invention is to provide an alternative diagnostic method of a particulate filter in an exhaust line using a downstream soot sensor.

SUMMARY OF THE INVENTION

The present invention proposes a method for monitoring a particulate filter arranged in an exhaust line of an internal combustion engine, which comprises:
monitoring the exhaust gas stream downstream of the particulate filter by means of a downstream soot sensor;
monitoring the accumulation of soot at an upstream soot sensor over a respective sensor cycle of the downstream soot sensor.

The method then includes the step of deciding on the particulate filter operating status (e.g. faulty or functional) based on the information given by the downstream and upstream soot sensors.

In fact, the present invention proposes a diagnostic concept that does not require a limit particulate filter model but relies on a pair of soot sensors to assess the particulate filter performance.

As will be apparent below, the upstream soot sensor may be either an actual sensor or may be simulated.

The amount of accumulated soot at the upstream sensor may be determined based on the sensor cycles of the upstream soot sensor, and expressed either as a soot loading level (or soot indicator) or as a number or frequency of sensor cycles.

The term "sensor cycle" designates in the context of the present invention the active phase of the soot sensor, during which the sensor is able to measure the soot amount, hence extending from the start of the accumulation until the sensor reaches its threshold value. A sensor cycle thus typically follows a regeneration phase and is completed when the sensor signal reaches a predetermined threshold. The length of the sensor cycle corresponds to the sensor response time.

Whereas prior art solutions have mainly tried to estimate an expected sensor cycle time at the particulate filter outlet, the present invention is based on the estimation of soot accumulation upstream of the particulate filter, which is similar to estimating the response of a soot sensor located before the particulate filter. Let us suppose a configuration where two soot sensors with same detection characteristics (e.g. resistive sensors having a sensor response time inversely proportional to the soot amount and same detection threshold) are placed before and after a particulate filter with good efficiency. The upstream soot sensor should undergo a number of cycles while a single sensor cycle is measured downstream. This will be more apparent from the following equation:

$$\eta = PF \text{ efficiency}(\%) \qquad \text{(eq. 1)}$$
$$= 1 - \frac{nbr \text{ cycles downstream}}{nbr \text{ cycles upsteam}}$$

which expresses the particulate filter efficiency in function of the number of soot sensor cycles downstream of the particulate filter (nbr cycles downstream) and the number of soot cycles upstream (nbr cycles upstream).

For example, for a particulate filter with 90% efficiency, the upstream sensor should react 10 times (i.e. complete 10 sensor cycles) while the downstream sensor undergoes only one cycle.

Accordingly, in one embodiment of the present method, the efficiency of the particulate filter is computed from the respective number of sensor cycles for a given observation period, preferably from equation 1, and this efficiency value is then used for the purpose of particulate filter diagnostic. This approach is particularly easy to implement when an actual sensor is used before the particulate filter. Preferably, efficiency is computed for an observation period of one sensor cycle of the downstream soot sensor.

In another embodiment, inspired from this accumulation principle, the method relies on the determination of a soot indicator that is representative of the loading level or accumulated soot amount at the upstream soot sensor, during the sensor cycle of the downstream soot sensor. The soot indicator may indicate the amount of accumulated soot with respect to any desired scale or unit, e.g. as a percentage.

The soot sensor is typically reinitialized before a new sensor cycle is started, and the estimation of the soot indicator is computed with respect to the start of the sensor cycle of the downstream soot sensor.

The determination of the soot indicator can be based on measurement (by an upstream sensor) or by simulation, or both. In practice, simulation is preferred for the economy of components. It also avoids placing a soot sensor in the harsh environment at the outlet of the engine.

The determination of the soot indicator advantageously involves a model having as input values a number of predetermined engine operating parameters, such as the concentration of the engine-out soot and the exhaust gas velocity. These parameters allow calculating and estimating the soot flow upstream of the particulate filter.

The model may comprise a transfer function simulating a soot sensor placed upstream of the particulate filter and that is outputting a model response time for this upstream virtual sensor, preferably corresponding to the response time in steady state for the current engine operating parameters (i.e. as if current engine operating conditions stayed constant during a complete PM sensor cycle) The model computes the soot indicator iteratively, during the sensor cycle of the downstrean soot sensor. The soot indicator is computed based on the portion of model sensor cycle time corresponding to each iteration period.

Hence, the soot indicator, which is typically updated periodically, provides a real time determination of the accumulated amount of soot upstream of the particulate filter.

For the particulate filter diagnostic, the soot indicator may then be compared to at least one threshold calibrated to detect a satisfactorily operating particulate filter. For example, the soot indicator is periodically compared to a pass threshold and a fail threshold that are calibrated to reach the desired detection threshold; the use of two distinct threshold improves robustness. However, the pass and fail threshold could have the same value.

To further improve the robustness of the diagnostic, since the method is impacted by artifacts, measurement errors, etc, a PASS or FAIL status is preferably only reported as a decision when an average value of prior soot indicator values (stored in a buffer) is above the Pass threshold or below the Fail threshold.

According to another aspect, the present invention relates to a system for monitoring a particulate filter arranged in an exhaust line of an internal combustion engine, the system comprising a downstream soot sensor arranged after the particulate filter; and control means for implementing the above described method.

According to a further aspect, the present invention concerns a computer program comprising processor-implementable instructions, which, when executed by a processor, cause said processor to carry out the above described method.

BRIEF DESCRIPTION OF THE DRAWINGS

The present invention will now be described, by way of example, with reference to the accompanying drawings, in which:

FIG. 1: is a principle drawing of an engine with an exhaust line provided with a number of exhaust after treatment devices;

FIG. 2: is a principle graph representing the reaction vs. time of both a virtual soot sensor located upstream of the PF and a soot sensor located downstream of the PF, where a peak represents the end of the sensor cycle for the concerned sensor;

FIG. 3: is a principle graph depicting (over time) the reaction of a downstream soot sensor and the soot indicator (indicated Loading Level) estimation, for a particulate filter having 90% efficiency;

FIGS. 5A-5C: show a set of graphs where the soot indicator (PMS Loading Level) in function of the time for a properly working particulate filter is shown in FIG. 5B and the soot indicator in function of the time for a faulty particulate filter is shown in FIG. 5C, whereas FIG. 5A shows the corresponding vehicle speed during a test cycle.

DETAILED DESCRIPTION OF A PREFERRED EMBODIMENT

Figure 4:
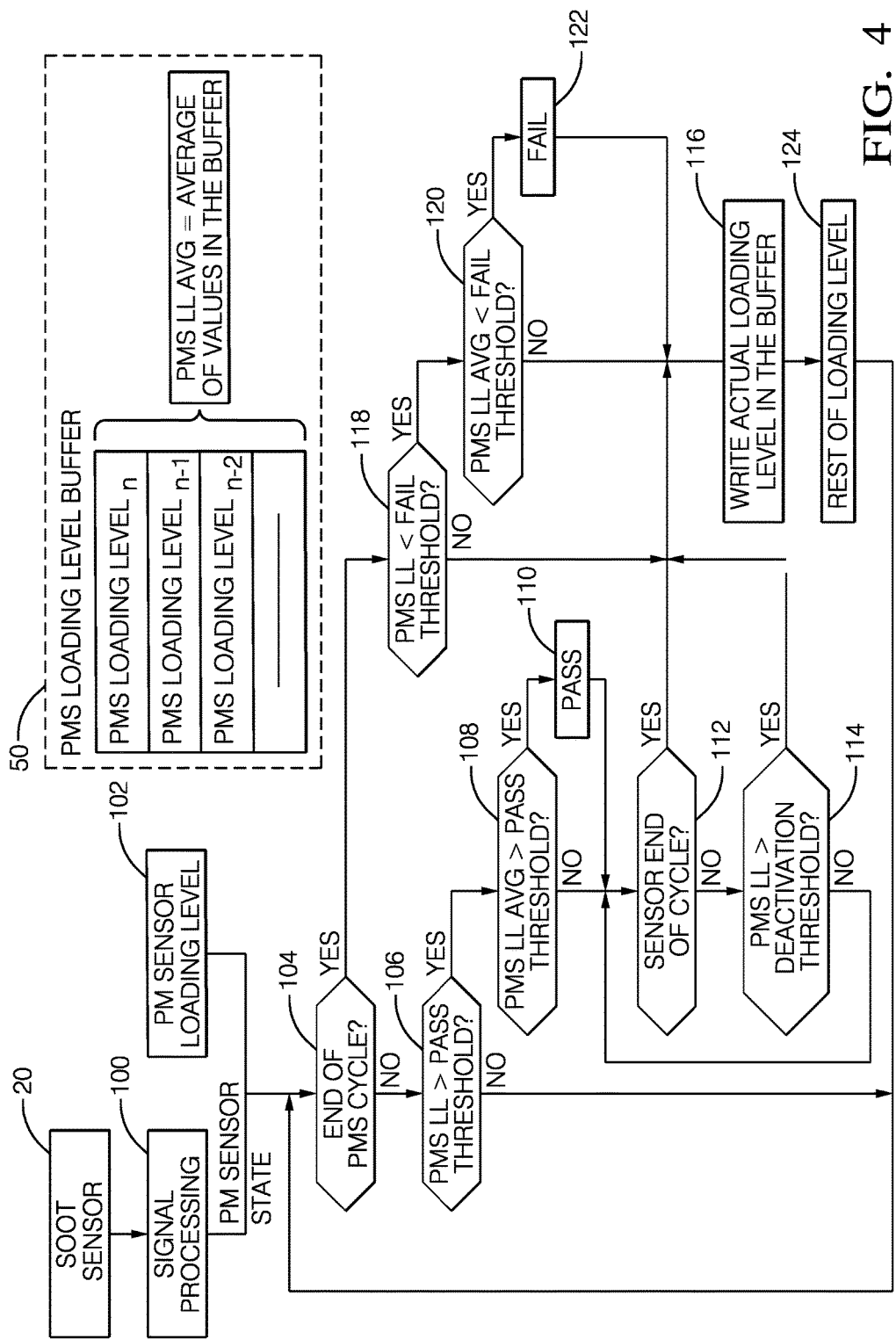
FIG. 4: is a flowchart of an embodiment of the present diagnostic method.

FIG. 1 shows an exhaust piping system 10 connected to an internal combustion engine 12, e.g. a multi-cylinder diesel engine, which generates an exhaust gas stream containing soot and/or particles and other pollutants. An Engine control unit (ECU—not shown) is signally and operatively connected to a number of sensors and actuators for controlling and monitoring engine operation, as it is known in the art.

The exhaust piping system 10 typically comprises a turbocharger turbine and an exhaust gas recirculation valve (not shown) as well as a series of exhaust after treatment devices to reduce pollutant emissions. Specifically, the exhaust line 10 comprises here: an oxidation-promoting catalytic device 14 (hereinafter Diesel Oxidation Catalyst—DOC), followed by a particulate filter 16 (hereinafter Diesel Particulate Filter—DPF) and a $NO_x$ after-treatment device such as a Selective Catalytic Reduction (SCR) device 18.

Such exhaust after treatment devices are well known in the art and will therefore be herein only briefly described.

The DOC 14 is an oxidation promoting catalyst device that breaks down pollutants in the exhaust stream into less harmful components. More specifically, carbon monoxide (CO) and hydrocarbons (HC) are oxidized, as well as hydrocarbons that desorb from particulate matter (soot) and thus reduce the particle mass. Furthermore, a certain proportion of NO contained in the exhaust stream is oxidized into $NO_2$. The DOC 14 typically consists of a ceramic substrate structure, an oxidation mixture ("washcoat") and of the catalytically active precious metal such as platinum, palladium or rhodium.

The SCR catalyst 18 removes nitrogen oxides ($NO_x$) through chemical reaction between the exhaust gases, a reducing agent, and a catalyst (e.g. vanadium based catalysts in heavy duty vehicles or Zeolite based catalysts on passenger cars). Urea-based SCR catalysts, for example, use gaseous ammonia as the active NOx reducing agent. Typically, an injection system is used to supply urea into the exhaust gas stream entering the SCR catalyst where it decomposes into gaseous ammonia (NH3) and is stored in the catalyst. The NOx contained in the engine exhaust gas entering the catalyst then reacts with the stored ammonia, which produces nitrogen and water.

The DPF 16 is designed to remove diesel particulate matter and/or soot from the exhaust gas. Current DPFs are based, e.g., on a honeycomb filter structure made from silicon carbide or Cordierite with a large number of parallel channels; or on sintered metal filters comprising a metallic carrier structure composed of mesh filled with sintered metal powder. The DPF may alternatively be of the catalyzed-type, referred to as CDPF.

As it is well known, the growing amount of soot/particulate matter deposited in the DPF 16 gradually increases the exhaust back pressure. The DPF 16 must therefore be regularly regenerated, which implies burning off the soot that has collected. In passenger cars this is quite conventionally done by so-called "active regeneration", which involves raising the temperature of the exhaust gas and thus of the DPF 16 to about 550 to 600° C. in order to oxidize the particulate matter with oxygen present in the exhaust gas.

An on-board diagnostic scheme for monitoring the operating status of a particulate filter such as DPF 16 will now be described in detail with reference to the Figures.

Reference sign 20 designates a soot sensor (also referred to in the art as particulate matter sensor) installed after the DPF 16 in order to monitor the soot concentration in the exhaust gas stream exiting the DPF 16. The soot sensor 20 is here located between DPF 16 and SCR 18, but could also be arranged after the SCR catalyst 18.

The soot sensor 20 may be generally of the resistive type. For example, the soot sensor may be based on a multi-layer ceramic technology and comprise a sensor element with inter-digitated electrodes with an initially infinite electrical resistance.

During sensor operation soot particles are collected onto the sensing element and form conductive paths between the electrodes. The accumulated soot particles are eliminated by burning in a regeneration phase, before a new measuring cycle starts. The sensor also preferably includes a controllable heating element to perform regeneration actively.

The soot sensor can thus be designed as an integrating-type sensor providing an output signal that is function of the accumulated soot on the sensing element; and which is periodically regenerated to remove particulates from the sensor element.

In practice, the sensor is regenerated when the sensor output signal (e.g. current, but could be voltage or resistance) reaches a pre-determined threshold (based e.g. on criteria such as operating conditions, manufacturer information or as a design decision).

The actual measuring period of the sensor, i.e. basically from time $t_{start}$ (freshly regenerated sensor) up to the moment and during which the soot accumulates and the sensor current is determined, up to the reaching of the current threshold at $t_{End}$ is herein referred to as the "active phase". This active period of the sensor may also be referred to as "sensor cycle"; one sensor cycle corresponds to a full accumulation during the active phase, from $t_{start}$ to $t_{end}$. The time required for the sensor to reach the predetermined current threshold (from $t_{start}$ to $t_{end}$) is generally referred to as the "response time" of the sensor, and thus corresponds to a known soot amount.

Such resistive soot sensors are known in the art (from Ochs et al. cited above and from others) and need not be described in detail herein.

From the control perspective, it is convenient for the sensor to generate a sensor status information in addition to the sensor signal varying in relation to the amount of particulate matter in the exhaust stream.

For example, the sensor state may include a sensor regeneration status flag (0 or 1) to identify a regeneration phase, a sensor active flag (0 or 1) to identify the active phase, and a sensor self-diagnostic flag (0 or 1), all of which are used to indicate whether the soot signal is valid and thus useable for monitoring the DPF 16. When the sensor state is valid, it indicates that the soot sensor 20 is actively monitoring soot output from the DPF 16 (sensor active flag=1), and that the soot signal is valid and useable (sensor not regenerating and self-diagnostic passed successfully).

The soot sensor 20 may generally be connected to a sensor control unit (SCU), which is itself in charge of the signal processing and management, and namely for analysing the sensor signal and generating the sensor status. The sensor status is transmitted by the SCU, via e.g. a CAN-BUS, to the engine control unit ECU. The ECU may then be configured to carry out the particulate filter diagnostic scheme according to the present method.

It will be appreciated that the present method for monitoring a particulate filter employs a soot indicator representative of the accumulated soot amount upstream of the the particulate filter, which can be determined by means of an upstream soot sensor or by estimation. In the following, the determination of the soot indicator is advantageously done by estimation, to save for an additional soot sensor.

The present method adopts a strategy based on the estimation of soot accumulation upstream of the particulate filter, which can be considered similar to estimating the response of a soot sensor located before the particulate filter (but here in fact a virtual soot sensor).

The greater the efficiency of the particulate filter, the greater the accumulated soot mass—and thus the greater the magnitude of the soot indicator, for a given sensor cycle of the downstream soot sensor.

The principle of a sensor cycle based efficiency determination can be understood from FIG. 2, which is a principle graph where each peak 24 corresponds to the soot sensor reaching the current threshold, i.e. completing a sensor cycle. Time (t) is indicated in seconds and the vertical axis is graduated in arbitrary values 0 and 1. Starting from a time t=0, the upstream sensor reacts 10 times until t=600 s (i.e. 10 sensor cycles), where the PM sensor installed after the PF reacts for the first time (represented by the thicker curve 26).

The corresponding efficiency can be computed according to Eq (1):

$\eta = 1 - 1/10 = 0.9$ and thus corresponds to an efficiency of 90%.

The same behaviour is then observed over the following 600 s, i.e. up to t=1200 s.

Preferably, the soot indicator is an estimation of the soot loading of the virtual soot sensor rather than a number of soot sensor cycles, but the soot sensor scale range can be designed to also reflect the number of soot sensor cycles. In the graph of FIG. 3 e.g., the soot indicator is expressed in %, where 100% increase would correspond to completing a sensor cycle, i.e. one peak 24 in FIG. 2, but the current value nevertheless gives is representative of the instantaneous accumulated soot amount.

In conditions similar to those of FIG. 2 and considering a particulate filter with 90% efficiency, one can thus observe a soot indicator value of 1000% in FIG. 3 when the downstream soot sensor reacts for the first time at 600 s.

As can be understood from FIG. 3, the soot indicator is preferably periodically determined and thus gives a fairly continuous indication of the soot level at the virtual upstream soot sensor.

It may be noticed here that in the Figures, the soot indicator is named "Loading Level", "PM Sensor Loading Level" or "PMS LL".

Figure 6:
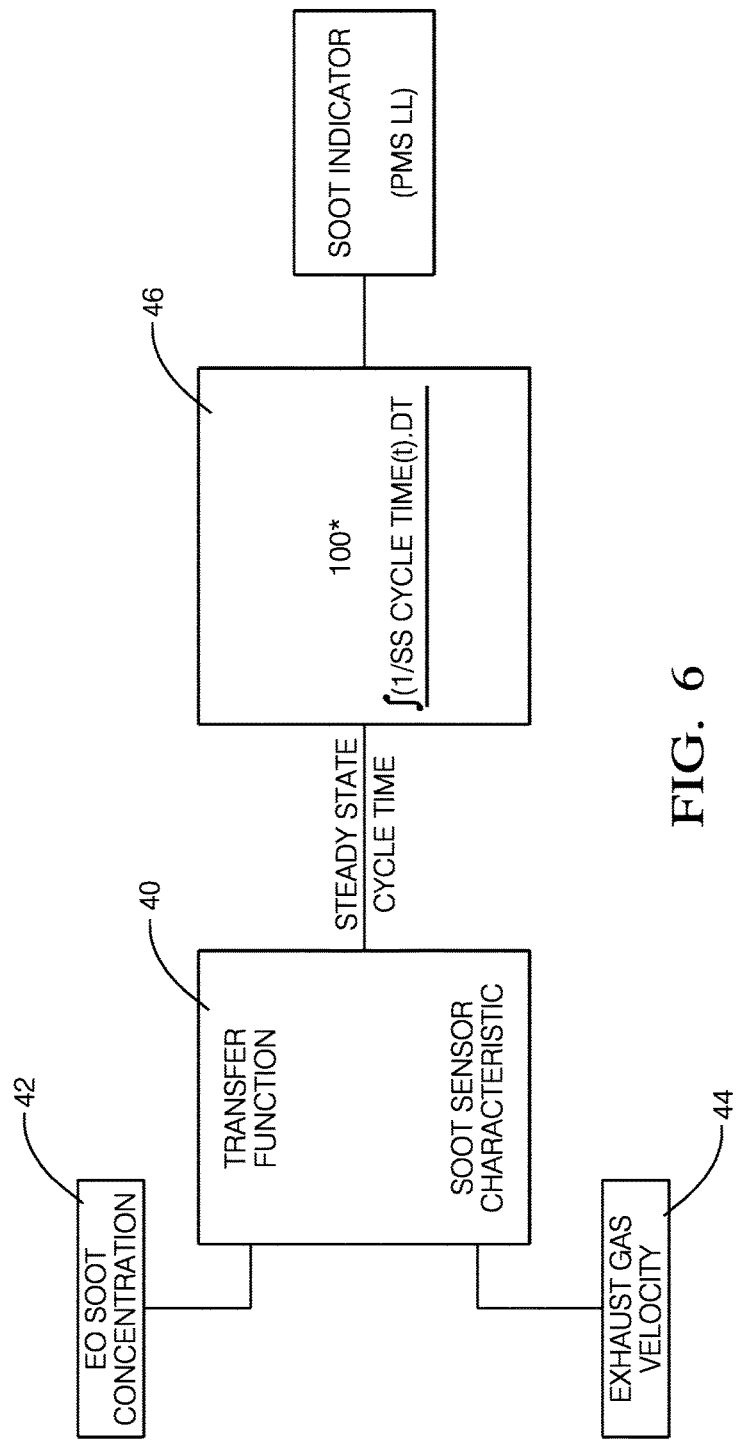
FIG. 6: is a diagram of the virtual sensor model computing the soot indicator.

One possible way of determining the soot indicator is illustrated in FIG. 6, wherein the soot indicator is calculated based on a model comprising a transfer function 40 simulating a soot sensor placed upstream of the particulate filter and outputting a sensor cycle time (SS cycle time(t)) in steady state (cycle time if current conditions would stay constant during a complete soot sensor cycle). The model has as input a number of predetermined engine operating parameters, in particular the concentration of engine-out soot (box 42) and the exhaust gas velocity (box 44). This model calculating the SS cycle time can be based either on formulas or on maps, or both. Other influencing parameters can be taken into account to improve the model accuracy.

The soot indicator is calculated by integration over time, from the virtual soot sensor cycle time, and expressed as a percentage via equation (2) (see also box 46):

$$\text{soot indicator(Loading Level \%)} = 100 \cdot \int_{tStart}^{tEnd} \frac{1}{SS \text{ cycle time}(t)} dt \quad (2)$$

The loading level gives a direct estimation about the overall amount of soot that has been accumulated upstream of the particulate filter in the virtual soot sensor.

Since the soot indicator in the present method is determined with respect to the sensor cycle of the downstream sensor, it will be reset before the beginning of a new sensor cycle (to be at 0% at $t_{start}$ of a new active phase).

FIG. 4 shows a flowchart of an embodiment of a diagnostic algorithm according the present method, based on the information obtained from the downstream soot sensor and soot indicator.

The main inputs of the diagnostic scheme are:
the status of the soot sensor 20, given by the signal processing device (box 100), e.g. sensor active flag (0 or 1), regeneration flag (0 or 1). The main information of interest here is to know whether the sensor cycle has been completed or not (can e.g. be determined by a switch from active flag to regeneration flag).
the current value of soot indicator (PM Sensor Loading Level-box 102) obtained from the model.

The method also uses the following parameters:
"FAIL threshold": a value below which the particulate filter is considered to be faulty;
"PASS threshold": a value above which the particulate filter is considered to operate properly (functional);
"Deactivation threshold": a value above which the soot sensor is deactivated;
"PMS LL avg": is the average value of a number of last determined soot indicator values stored in a buffer memory indicated 50. The values stored in this buffer 50 are soot indicator values determined during prior implementations of the method shown in FIG. 4, and written in the buffer as per box 116. PMS LL avg gives an indication of the recent trend of the particulate filter performance.

Let us suppose that we are at time $t_{start}=0$ indicating the start of a new sensor cycle (start of active phase). The routine of FIG. 4 is started for one monitoring period and input values and tests are run periodically, e.g. every 100 ms, or every second or any appropriate periodicity.

An initial test of the routine is at diamond 104, which determines, on the basis on the soot sensor status information, whether the sensor cycle is finished. The response to this test is NO, as long as the soot sensor has not reached its current threshold (i.e. as long as the sensor cycle is not complete).

So, during the accumulation period, the response to diamond 104 is NO, and the test of box 106 checks whether the current soot indicator value (PMS LL) is greater than the PASS threshold.

If it is not the case, then the routine closes the loop back to the entrance of diamond 104.

If the answer to diamond 106 is yes, then the current soot indicator value may be considered to indicate that the PF has passed the diagnostic test. However, in order to take into account measurement errors, the average soot indicator PMS LL avg is also compared to the Pass Threshold (box 108). If test 108 is satisfactory (PMS LL avg>Pass Threshold), then it is definitely concluded to a valid/functional PF (PASS flag activated at 110).

Downstream of test box 108 is a waiting loop based on box 112 that awaits the end of the sensor cycle, after which the last computed value of soot indicator is stored in the buffer 50 as latest value of soot indicator for the PF.

This waiting loop is interrupted by test 114 in case the current soot indicator value exceeds a deactivation threshold. In such case, the monitoring is stopped to save the downstream soot sensor lifetime and the last computed value of soot indicator is stored in buffer 50.

If the soot indicator has not exceed the Pass threshold and the end of the soot sensor cycle is reached (YES at test 104), then the soot indicator is compared to the Fail Threshold.

If the soot indicator is below the Fail threshold, but also the average soot indicator PMS LL avg (test 120), then it is concluded to a faulty particulate filter (FAIL flag in box 122).

If the one of the tests 118 or 120 yields NO, then the last computed soot indicator value is simply stored in buffer 50.

Upon updating the buffer 50, the routine may be reset and in particular the soot indicator (loading Level), as indicated in box 124.

A few situations remain to be noted. In case the sensor cycle is complete (Yes at test 104) and the soot indicator is above the Fail threshold (test 118 yields NO), then the soot indicator is simply written in the buffer 50 and no decision on the DPF operating status is taken. The monitoring of the DPF will continue by starting a new sensor cycle.

Also, no decision on the DPF status will be taken when test 108 yields NO, i.e. the average soot indicator value PMS LL avg is below the Pass threshold.

Furthermore, when a FAIL (122) decision is taken or when the soot indicator exceeds the Deactivation threshold (YES at box 114), the DPF monitoring may be interrupted and started again at the next driving cycle.

Figures 5A, 5B, 5C:
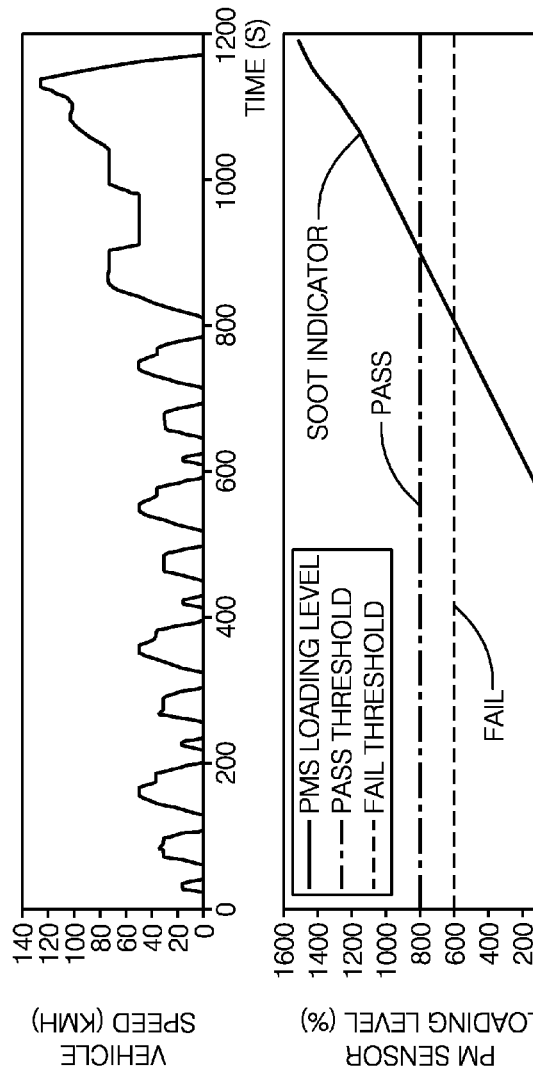

FIGS. 5B and 5C show two examples of the evolution of the soot indicator for a functional (properly operating) particulate filter (FIG. 5B) and a faulty particulate filter (FIG. 5C), where the diagnostic has been carried out by the present method.

FIG. 5A is a graph representing vehicle speed vs. time for a typical engine test cycle, from a cold start.

FIG. 5B hence shows the soot indicator evolution (PM sensor Loading Level) vs. time, as well as the PASS and FAIL threshold. FIG. 5B shows the loading level curve evolution in function of time. It can be seen that loading level remains at 0 until about 500 s; this is due to the cold start. Just after 500 s, the soot indicator starts rising, and increases continually over the shown time window (up to 1200 s). At t=800 s, the loading level curve crosses the "FAIL" threshold line before crossing the "PASS" threshold line at about 900 s.

The timing at which the soot indicator starts growing is indicated $t_{start}$, because as explained above estimation by means of the soot sensor starts together with the beginning of the sensor cycle of the downstream soot sensor (start of the activation phase). In the graph of FIG. 5B, the sensor cycle of the downstream soot sensor is not completed during the shown monitoring period of 1200 s; the driving cycle is finished so the engine and the sensor are switched off before reaching $t_{End}$. Also, the deactivation threshold was not reached (e.g. set at 1600%).

In case of a longer driving cycle, the loading level would have increased further until a deactivation threshold is reached or when the PM sensor cycle is finished.

The graph of FIG. 5C in turn concerns the case of a deficient DPF. The duration of the sensor cycle of the downstream soot sensor is indicated by $t_{start}$ and $t_{end}$. As can be seen, during the sensor cycle of the downstream soot sensor, the soot indicator remained below the FAIL threshold, indicating a faulty PF.

After $t_{end}$, the downstream soot sensor is regenerated and another measuring cycle starts.

The invention claimed is:

1. A method for monitoring a particulate filter arranged in an exhaust line of an internal combustion engine, said method comprising the steps of:
    monitoring the exhaust gas stream downstream of the particulate filter by means of a downstream soot sensor, said downstream soot sensor having a characteristic sensor cycle during which particulate matter accumulates up to a predetermined threshold;
    monitoring the accumulation of soot at an upstream soot sensor over a respective sensor cycle of the downstream soot sensor;
    deciding on the particulate filter operating status based on the information of the downstream and upstream soot sensors;
    wherein the upstream soot sensor has a characteristic sensor cycle during which particulate matter accumulates up to a predetermined threshold; and the amount of accumulated soot at the upstream sensor is determined based on the sensor cycles of the upstream soot sensor, and expressed either as a soot loading level or as a number or frequency of sensor cycles;
    wherein an efficiency of the particulate filter is computed from the respective numbers of sensor cycles for a given observation period from the equation:

$$\eta = 1 - \frac{nbrcyclesdownstream}{nbrcyclesupsteam},$$

where nbrcyclesdownstream is the number of sensor cycles of the downstream soot sensor and nbrcyclesupstream is the number of sensor cycles of the upstream soot sensor.

2. A method for monitoring a particulate filter arranged in an exhaust line of an internal combustion engine, said method comprising the steps of:
    monitoring the exhaust gas stream downstream of the particulate filter by means of a downstream soot sensor, said downstream soot sensor having a characteristic sensor cycle during which particulate matter accumulates up to a predetermined threshold;
    monitoring the accumulation of soot at an upstream soot sensor over a respective sensor cycle of the downstream soot sensor;
    deciding on the particulate filter operating status based on the information of the downstream and upstream soot sensors;
    wherein the upstream soot sensor has a characteristic sensor cycle during which particulate matter accumulates up to a predetermined threshold; and the amount of accumulated soot at the upstream sensor is determined based on the sensor cycles of the upstream soot sensor, and expressed either as a soot loading level or as a number or frequency of sensor cycles;
    wherein said upstream soot sensor is provided by a virtual sensor model having as input a number of predetermined engine operating parameters;
    wherein said model comprises a transfer function outputting a model sensor response time, corresponding to the response time in steady state corresponding to the current engine operating parameters.

3. The method as claimed in claim 2, wherein said engine operating parameters include at least the concentration of engine-out soot and exhaust gas velocity.

4. The method as claimed in claim 2, wherein a soot indicator representative of the soot loading level of the upstream soot sensor is iteratively computed based on the portion of model sensor cycle time corresponding to each iteration period, over one sensor cycle of the downstream soot sensor.

5. The method as claimed in claim 4, wherein the calculation of the soot indicator is implemented on the basis of the principle equation:

$$\text{soot indicator}(\%) = 100 * \int \frac{1}{SS \text{ cycle time}(t)} dt,$$

where SS cycle time (t) is the model sensor cycle time.

6. The method as claimed in claim 4 wherein the soot indicator is compared to:
    a pass threshold, which when exceeded indicates a functioning particulate filter;

and to a fail threshold, which if not exceeded, indicates a faulty particulate filter.

7. The method as claimed in claim 4 wherein the following routine is periodically performed:
   determining the status of the downstream soot sensor and the soot indicator at the current timing;
   if the downstream soot sensor has not finished its sensor cycle:
      comparing the soot indicator to a pass threshold, and if exceeded, comparing an average of prior soot indicator values to the pass threshold, and, if exceeded, the particulate filter is considered to have a functional operating status;
   or
   if the downstream soot sensor has finished its sensor cycle and the soot indicator is below a fail threshold:
      an average of prior soot indicator values is compared to the fail threshold, and, if below, the particulate filter is considered to have a faulty operating status.

8. The method according to claim 7, wherein the current soot indicator value is stored as the prior soot indicator value after the completion of the sensor cycle of the downstream soot sensor.

9. The method according to claim 7, wherein the current soot indicator value is stored as the prior soot indicator value when it reaches a predetermined deactivation threshold.

10. The method as claimed in claim 2 wherein soot accumulation at the upstream soot sensor is monitored over a period of one sensor cycle for the downstream soot sensor.

11. A system for monitoring a particulate filter arranged in an exhaust line of an internal combustion engine, said system comprising a downstream soot sensor arranged after the particulate filter;
   and control means configured for implementing the method according to claim 2.

* * * * *